United States Patent [19]

Yasuda et al.

[11] Patent Number: 5,457,201

[45] Date of Patent: Oct. 10, 1995

[54] CHIRAL RESOLUTION PROCESS

[75] Inventors: Nobuyoshi Yasuda, Mountainside; Ann E. DeCamp, Scotch Plains; Edward J. J. Grabowski, Westfield, all of N.J.

[73] Assignee: Merck & Co., Inc., Rahway, N.J.

[21] Appl. No.: 374,399

[22] Filed: Jan. 17, 1995

Related U.S. Application Data

[63] Continuation of Ser. No. 294,771, Aug. 23, 1994, abandoned, which is a continuation of Ser. No. 112,735, Aug. 27, 1993, abandoned.

[51] Int. Cl.$^6$ ............... A61K 31/505; C07D 239/80; C07D 239/82
[52] U.S. Cl. .......................... 544/284; 514/259
[58] Field of Search ............................... 544/284

[56] References Cited

U.S. PATENT DOCUMENTS

| | | | |
|---|---|---|---|
| 4,880,926 | 11/1989 | Fujiwara et al. | 544/105 |
| 4,978,666 | 12/1990 | Nohira et al. | 514/255 |
| 4,995,899 | 2/1991 | Scholz et al. | 71/92 |
| 5,025,010 | 6/1991 | Oekonomopulos et al. | 514/224.2 |
| 5,247,090 | 9/1993 | Brickner | 546/89 |

FOREIGN PATENT DOCUMENTS 440372  8/1991  European Pat. Off. .

OTHER PUBLICATIONS

Staal et al., AIDS Research and Human Retroviruses, 9(4) (1993) 299–306.
Flexner et al., Antimicrobial Agents and Chemotherapy, 35(12) (1991) 2544–2550.
Antiviral Agents Bulletin, 6(8) (Aug. 1993) 231.
Antiviral Agents Bulletin, 6(6) (Jun. 1993) 162–163.
Antiviral Agents Bulletin, 6(8) (Aug. 1993) 228.
Merck Standby Statement of Sep. 14, 1993.
Saari et al., Journal of Medicinal Chemistry, 35 (1992) 3792–3802.
Dr. Sandstrom Letter of Jun. 19, 1990.
Mansuri et al., Chemtech, (Sep. 1992) 564–572.
Saunders, Drug Design and Discovery, 8, (1992) 255–263.
Connolly et al., Antimicrobial Agents and Chemotherapy, 36(2) (Feb. 1992) 245–254.
De Clercq, AIDS Research and Human Retroviruses, 8(2) (1992) 119–133.

*Primary Examiner*—Mukund J. Shah
*Assistant Examiner*—Matthew V. Grumbling
*Attorney, Agent, or Firm*—Roy D. Meredith; Jack L. Tribble

[57] ABSTRACT

A chiral resolution process is described for the purification of a substituted chiral quinazoline, by salt formation with a resolving agent, followed by crystallization.

6 Claims, No Drawings

CHIRAL RESOLUTION PROCESS

This is a continuation of application Ser. No. 08/294,771 filed on Aug. 23, 1994 now abandoned, which is a continuation of application Ser. No. 08/112,735 filed on Aug. 27, 1993 now abandoned.

SUMMARY OF THE INVENTION

A chiral resolution process is described for the purification of a substituted chiral quinazoline, by salt formation with a resolving agent, followed by crystallization.

BACKGROUND OF THE INVENTION

This application is related to Merck case 18727, U.S. Ser. No. 07/880,119, filed May 7, 1992, and to its continuation-in-part, Merck case 18727IA, U.S. Ser. No. 07/991,164, filed Dec. 16, 1992.

This invention relates to an improved process for synthesizing the AIDS antiviral L-738,372, which is a chiral compound having novel requirements in the crystallization step(s) of its improved synthesis.

The substituted quinazoline L-738,372 is an exceptionally potent inhibitor of HIV reverse transcriptase. This activity of the compound makes it useful in the treatment or prevention of AIDS. The present invention describes an improved synthesis of this compound.

Separating the enantiomers of the asymmetric carbon at position 4 is the penultimate or final step in the synthesis of the compound. Previous attempts use derivatization in lower yield, e.g., reaction with 1(S)-camphanic chloride as illustrated in Example 7. The disadvantages of camphanyl derivatization include the expense of the reagent, the need for two equivalents in the reaction, a chromatographic step to separate the non-crystalline diastereomeric derivatives, as well as a two step removal of the camphanate groups. In contrast, the advantages of the present method include the formation of a salt instead of a derivative, and substantially higher yields. Further, the present method is practical and amenable to scale up.

It is commonly known that crystallization is an unpredictable science. In this application, a novel and unexpected process of chiral resolution of the substituted quinazoline is achieved by a series of crystallizations.

DETAILED DESCRIPTION OF THE INVENTION

A method is disclosed for the chiral resolution in the synthesis of the compound 1-738,372, of the structure

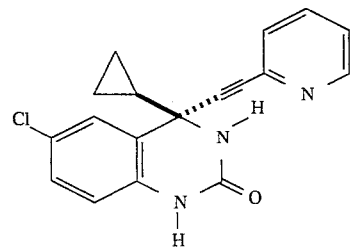

comprising the steps of, a) providing one equivalent of N-protected racemate of the formula

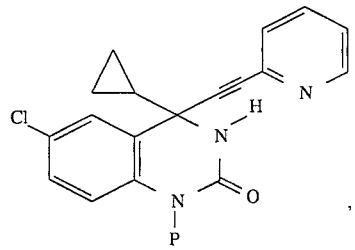

wherein P is a protecting group, and P is defined as —CH$_2$—A, and A is i) phenyl unsubstituted or substituted one or more times with B, wherein B is C$_{1-4}$alkyl, C$_{1-4}$alkoxy, or halo;
ii) naphthyl unsubstituted or substituted one or more times with B;
iii) anthryl unsubstituted or substituted one or more times with B;

b) adding in solution about 0.5–2.0 equivalents of a resolving agent to form a salt, said resolving agent selected from the group consisting essentially of (1R)-(−)-10-camphorsulphonic acid, (1S)-(+)-10-camphorsulfonic acid, (1R)-(endo,anti)-(+)-3-bromocamphor-8-sulfonic acid, or (1S)-(endo,anti)-(−)-3-bromocamphor-8-sulfonic acid, or salts or hydrates thereof;

c) purifying the desired stereoisomer by crystallization in the presence of ester solvent;

d) removing the protecting group to give L-738,372.

In one preferred embodiment of this invention, P is paramethoxy benzyl, the ester solvent is butyl acetate, and the resolving agent is (1S)-(+)-10-camphorsulfonic acid, as also illustrated in the following scheme.

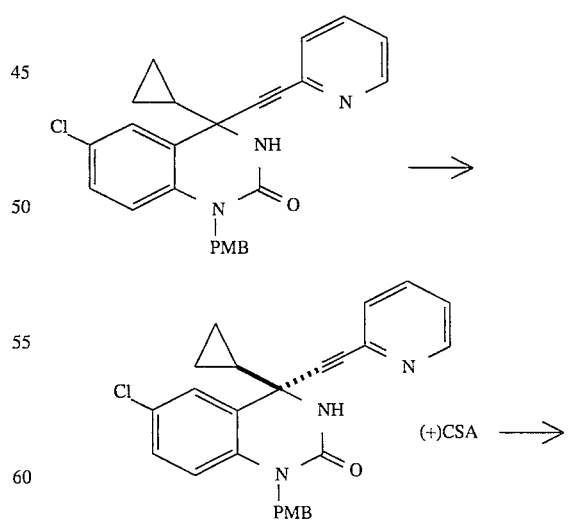

-continued

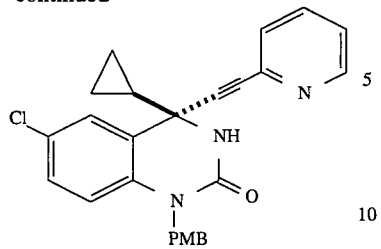

In a second preferred embodiment of this invention, P is para-methoxybenzyl, the ester solvent is butyl acetate, and the resolving agent is (1R)-(−)-10-camphorsulphonic acid.

In a third preferred embodiment, P is 9-anthrylmethyl, the solvent is butyl acetate or THF, and the resolving agent is (1S)-(+)-10-camphorsulphonic acid.

In a fourth preferred embodiment, P is 9-anthrylmethyl, the solvent is butyl acetate or THF, and the resolving agent is (1R)-(−)-10-camphorsulphonic acid.

In this invention, the term racemate is intended to cover a mixture of stereoisomers, but it need not be exactly 50:50. Halo covers fluoro, chloro, bromo and iodo.

The chiral resolution process of the present invention begins with the initial mixing of solvent with racemic N-protected L-738,372. Useful solvents include, but are not limited to, THF, methylene chloride, toluene, acetonitrile, methanol, ethanol, isoamyl alcohol, DMF, DMF H$_2$O, hexane, butyl acetate, ethyl acetate, isopropyl acetate, methyl acetate, butyl propionate, ethyl propionate, isopropyl propionate, or methyl propionate. When the protecting group is para-methoxybenzyl, only the ester solvents have been found to function well as recrystallization solvents. When the protecting group is anthryl, THF as well as the ester solvents have been found to be suitable as recrystallization solvents. In order to avoid a solvent switch before crystallization, the preferred solvent type for initial mixing of racemic N-protected L-738,372 is an ester solvent, but THF is a suitable alternative solvent for anthryl protected compounds. The most preferred ester solvent is butyl acetate, due to its high boiling point.

Applicants have found that a protecting group at the N1 position is required for obtaining crystals in subsequent purification steps. Suitable protecting groups on the N1 include benzyl, napthylmethyl or anthrylmethyl groups, any of which may be substituted one or more times with $C_{1-4}$alkyl, $C_{1-4}$alkoxy, or halo. A preferred protecting group is para-methoxy benzyl, abbreviated PMB. Another preferred group is 9-anthrylmethyl. Anthryl is the radical corresponding to anthracene. Applicants have also found that other protecting groups do not function well in the present chiral resolution process, e.g., benzhydryl, trityl or silicon-substituted protecting groups.

After initial mixing of racemic N-protected L-738,372 with solvent, the mixture may be heated to dissolve the compound, if necessary. For dissolving the compound, a temperature in the range of about room temperature to about 80° C. is needed. This heating step may succeed the next step of adding resolving agent. For the ester solvent butyl acetate, heating to about 80° C. is permitted.

About 0.5–2.0 equivalents of resolving agent are added to the racemic N-protected L-738,372. Various resolving agents are suitable for the salt formation and chiral resolution of the present invention. Since the pyridine moiety is a weak base, a strong acid group is desirable. Appropriate resolving agents include, but are not limited to, the following:

(1R)-(−)-10-camphorsulphonic acid,
(1S)-(+)-10-camphorsulphonic acid,
(1R)-(endo, anti)-(+)-3-bromocamphor-8-sulphonic acid, or
(1S)-(endo, anti)-(−)-3-bromocamphor-8-sulphonic acid, or salts thereof or hydrates thereof. The preferred resolving agent is (1S)-(+)-10-camphorsulphonic acid, abbreviated (+)-CSA. Another preferred resolving agent is (1R)-(−)-10-camphorsulphonic acid, abbreviated (−)-CSA.

Further heating may be advisable at this point to drive the reactants into solution. The spontaneous formation of the diastereomeric salt is allowed to cool gradually to allow crystal formation after seeding. The salt is typically isolated by filtration.

A solvent switch before salt formation with resolving agent may be necessary to dissolve the N-protected racemate salt in an ester solvent suitable for crystallization. This is accomplished at different points in the process by, e.g., drying and redissolving.

In the crystallization process, applicants have found that when the protecting group is PMB, with (+)-CSA as resolving agent and butyl acetate as the ester solvent, that the correct diastereomer crystallizes out in about the first 12 hours after salt formation, but thereafter a mixture of both diastereomers crystallizes out.

Examples 1–6 illustrate a synthesis of racemic L-738,372. Examples 7–8 illustrate chiral resolution by derivatization with (1S)-(−)-camphanic chloride. Example 9 illustrates the new resolution procedure of the present invention, by salt formation from (1S)-(+)-10-camphorsulphonic acid.

EXAMPLE 1

4-Chloro-2-cyanoaniline

A 2 L round bottom flask was charged with 138 g (1.168 mol) of anthranilonitrile (Aldrich) and 1.05 L of acetonitrile. The flask was heated to 50° C. and 172.5 g (1.29 mol) of N-chlorosuccinimide (Aldrich) was added in one portion. The reaction was heated at reflux for 2.0 h (HPLC monitoring), cooled to approx. 35° C., and the solvent is removed by rotovap at reduced pressure. The residue was partitioned between 1.5 L ethyl acetate and 1 L cold water. The aqueous layer was extracted with ethyl acetate and the combined organic layers washed with 3 portions of cold water, brine, dried over MgSO$_4$ and treated with activated carbon. The solvent was removed by rotovap at reduced pressure to give a pale orange solid which was crystallized from 430 mL of hot 1-chlorobutane and allowed to cool to room temp. overnight. After filtration, the resulting crystals were washed with cold butylchloride and air dried to give 82.5 g of off-white crystals (94% pure by HPLC). This material was recrystallized from 140 mL of s chlorobutane and 125 mL hexane to give 73 g (41%) of the title compound as a colorless solid. An additional 18.8 g (10.5%) was obtained from two recrystallizations of material from the mother liquors.

EXAMPLE 2

6-Chloro-4-cyclopropylquinazolin-2(1H)-one

A 3-necked round bottom flask equipped with a thermometer, magnetic stirrer, addition funnel and septum inlet was oven dried and swept with Ar. The flask was charged with a suspension of 5.5 g (0.226 g-atom) of magnesium turnings (Aldrich) in 150 mL of dry THF. A 3.0 mL portion of cyclopropyl bromide (Aldrich, distilled) was added to the suspension in one portion, and the mixture heated to 33° C., at which time a gentle exotherm began. After this exotherm had stabilized at 48° C., the remaining 15.8 mL (0.235 mol total) of cyclopropyl bromide was added dropwise as a solution in 30 mL of dry THF to maintain an internal temperature of 48°–52° C. After the addition, the solution was kept at that temperature for 45 min using a heating mantle. (Note: 20 mL of this Grignard solution was removed via cannula for another reaction). A solution of 10.0 g (0.066 mol) of 4-chloro-2-cyanoaniline in 50 mL of dry THF was added dropwise at a rate which maintained an internal temperature of 47°–50° C. This temperature was maintained for 30 min after the addition was complete using a heating mantle. A 17.4 mL (0.206 mol) quantity of dimethylcarbonate (Aldrich) was added dropwise at a rate which maintained the temperature at 48°–55° C. After the addition, the reaction was kept at this temperature for 30 min using a heating mantle. The reaction solution was cooled to 25° C. and poured into a rapidly stirred mixture of ice and 500 mL of 1M citric acid. This mixture was extracted with two portions of $CHCl_3$, the combined organic layers washed with 10% $Na_2CO_3$, dried over $MgSO_4$, concentrated to a volume of approx. 450 mL and stored in the refrigerator under Ar overnight which caused the product to crystallize. The crystals were filtered and washed with cold $CHCl_3$ to give 6.5 g (44%) of the title compound as a pale yellow solid. Chromatography of the mother liquors on 850 g of fine $SiO_2$ using 35:1 $CHCl_3$—$CH_3OH$ provided an additional 5.2 g (35%).

EXAMPLE 3

6-Chloro-4-cyclopropyl-1-(p-methoxybenzyl) quinazolin-2(1H)-one

To a 0° C. solution of 9.0 g (0.04 1 mol) of 6-chloro-4-cyclopropylquinazolin-2(1H)-one in 150 mL of dry DMF (Aldrich Sure-Seal) under Ar was added 42.5 mL of a 1.0M solution of lithium bis(trimethylsilyl)amide in hexane dropwise. After the addition, 8.14 mL (0.06 mol) of p-methoxybenzyl chloride (Aldrich) was added in one portion, and the flask immersed in an oil bath maintained at 55°–60° C. The reaction was heated for 12.5 h, then allowed to stand at room temperature overnight. The solvents were removed by rotovap at reduced pressure and the residue partitioned between $CHCl_3$ and cold 1M citric acid. The aqueous layer was extracted with $CHCl_3$ and the combined organic layers washed with 10% $Na_2CO_3$, dried over $MgSO_4$. After removal of the solvents by rotovap at reduced pressure, the residue was triturated with ether to give 10.5 g (75%) of the title compound as a light yellow solid.

EXAMPLE 4

6-Chloro-4-cyclopropyl-4-ethynyl-3,4-dihydro-1-(p-methoxybenzyl)-quinazolin-2(1H)-one A suspension of 5.0 g (0.0147 mol) of 6-chloro-4-cyclopropyl-1-(4-methoxybenzyl)-quinazolin-2 (1H)-one and 14.19 g (0.044 mol) of magnesium triflate (Aldrich) in 160 mL of ether (Mallinckrodt) was stirred at room temp. under N2 for 30 min. In a separate flask, a –78° C. solution of 6.09 mL (4.32 g, 0.044 mol) of trimethylsilylacetylene (Lancaster) in 130 mL of ether was treated dropwise with 17.6 mL (0.044 mol) of 2.5M n-butyllithium in hexane under N2. After stirring for 30 min at –78° C., this solution was added to the r.t. quinazolinone suspension in one portion via cannula. The resulting suspension was stirred at r.t. overnight. The reaction mixture was poured into 10% citric acid and extracted with two portions of ether. The combined organic layers were washed with water, brine, dried over $MgSO_4$ and the solvents removed by rotovap at reduced pressure to give approx. 7.0 g of an oil. This oil was dissolved in 200 mL of THF (Fisher) and stirred vigorously with 150 mL of 1M aq. KOH for 20 min. at room temp. The reaction was acidified with 3M HCl and extracted with two portions of ether. The organic layers were combined and washed with water, brine, dried over $MgSO_4$ and the solvents removed to give an oily yellow solid which was triturated with ether-hexanes, followed by trituration with acetonitrile to afford the title compound as a colorless solid. All of the trituration filtrates were combined, concentrated and retriturated with acetonitrile to give a colorless solid which provided a combined yield of 3.54 g (66%) of the title compound.

EXAMPLE 5

6-Chloro-4-cyclopropyl-4-ethynyl-3,4-dihydroquinazolin-2(1H)-one

A solution of 1.4 g (4.11 mmol) of 6-chloro-4-cyclopropyl-4-ethynyl-3,4 -dihydro-1-(p-methoxybenzyl)quinazolin-2(1H)-one in 5 mL of $CH_2Cl_2$ was treated with 10 mL of trifluoroacetic acid (Aldrich) under N2 overnight at r.t. The reaction was concentrated by rotovap under reduced pressure and the residue partitioned between ethyl acetate and 10% citric acid. The organic layer was washed with water, brine, dried over $MgSO_4$ and the solvents removed to give an oil which was flash chromatographed on $SiO_2$ using 95:5 $CHCl_3$—$CH_3OH$ to give a foam. Trituration of this material with ether gave 720 mg (80%) of the title compound as a colorless solid.

EXAMPLE 6

Racemic 6-chloro-4-cyclopropyl-3,4-dihydro-4-((2-pyridyl) ethynyl)-quinazolin-2(1H)-one (L-737,219)

A solution of 60 mg (0.24 mmol) of 6-chloro-4-cyclopropyl-4-ethynyl-3,4-dihydroquinazolin-2 (1)-one, 47 mg (0.3 mmol) of 2-bromopyridine (Aldrich), and 8.5 mg (0.012 mmol) of bis(triphenylphosphine) palladium dichloride (Aldrich) in 2 mL of 1:1 $CH_3CN$-triethylamine was stirred in a sealed robe at 80° C. overnight. After standing at r.t. for 48 h, the reaction was diluted with $CH_3CN$, filtered through a Celite pad, and concentrated to give an oily solid which was chromatographed on fine $SiO_2$ using 95:5 $CHCl_3$—$CH_3OH$. Trituration with ether-hexane provided 60 mg (77%) of the title compound as a colorless amorphous solid.

EXAMPLE 7

1,3-(Di-(1S)-camphanoyl)-6-chloro-4-cyclopropyl-3,4-dihydro-4-((2 -pyridyl)ethynyl)quinazolin-2(1H)-one A solution of 200 mg (0.618 mmol) of the product from Example 6, 134 mg (0.618 mmol) of (1S)-camphanic chloride, 76 mg (0.618 mmol) of N,N-dimethylaminopyridine (DMAP), and 0.43 mL (3.09 mmol) of triethylamine in 2.0 mL of $CH_2Cl_2$ was stirred under Ar at rt for 18 hours. An additional 76 mg (0.618 mmol) of DMAP and 268 mg (1.23 mmol) of (1S)-camphanic chloride was added to the reaction mixture, and stirring continued for 6 hours. The reaction was diluted with CHCl₃ and washed with 1M citric acid, water, 10% Na₂CO₃, dried over Na₂SO₄ and treated with activated carbon. Removal of the solvents gave a yellow foam which was chromatographed on 50 g fine SiO₂ using 1:2 EtOAc-hexane. The early eluting fractions were combined and evaporated to give 174 mg of diastereomer 1 as an almost colorless foam. Diastereomer 2 was obtained upon further elution as 138 mg of a foam. An analytical sample of diastereomer 2 was obtained by trituration from methanol; Calc'd for $C_{38}H_{38}ClN_3O_7$ C 66.71, H 5.60, N 6.14 Found C 66.38, H 5.53, N 6.17

EXAMPLE 8

(–)6-Chloro-4-cyclopropyl-3,4-dihydro-4-((2-pyridyl)-ethynyl)-quinazolin-2(1H)-one A solution of 143 mg (0.254 mmol) of diastereomer 1 from Example 7 in 1.0 mL of dimethoxyethane was treated with 0.4 mL of 1.0M aq. LiOH under Ar for 1.5 h. The reaction was partitioned between EtOAc and water. The aqueous layer was extracted with EtOAc and the combined organic layers were washed with water, brine, dried over MgSO₄, and the solvents removed to give 115 mg of a foam. This material was dissolved in 2.0 mL of ethanol, treated with 32 mg (0.168 mmol) of p-toluene sulfonic acid and heated at reflux under Ar for 64 h. The solvents were removed by rotary evaporation at reduced pressure and the residue partitioned between 10% Na₂CO₃ and EtOAc. The aqueous layer was extracted with EtOAc, and the combined organic layers washed with water, brine, dried over MgSO₄, treated with activated carbon, and the solvents removed to give a solid which was triturated with 1:1 Et₂O-hexane to provide 16 mg of the title compound as a pale yellow solid: NMR (CDCl₃) same as for Example 24; $\alpha_D$=–100° (c=0.4, CHCl₃).

EXAMPLE 9

Chiral Resolution

In a vessel is charged racemic 6-chloro-4-cyclolpropyl-4-[(2-pyridinyl)-2 -ethynyl]-3,4-dihydro-1-(4-methoxybenzyl)quinazolin-2(1H)-one (1.24g) and nBuOAc (100 mL). The suspension is heated to 80° C. to give a homogeneous solution. To the solution is added (+) camphorsulfonic acid (848 mg) and the mixture is refluxed for 30 minutes. The solution is gently cooled down to room temperature after seeding at 130° C. After aging at room temperature overnight, crystals are filtered off. [The purity at this point is typically 59% ee. After drying, 1.0 g of material is obtained].

The crystals are recrystallized from 80 mL of nBuOAc. The crystals are isolated by filtration to give 811 mg of the desired salt in 95% ee.

The crystals are recrystallized a second time from 70 mL of nBuOAc, isolated by filtration, dried in vacuo to give 765 mg of desired salt (i.e., of PMB-protected L-738,372 and (+)CSA).

EXAMPLE 10

Removal of Protecting Group

By the procedure of Example 5, the protecting group is removed from the product of Example 9.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. The compound

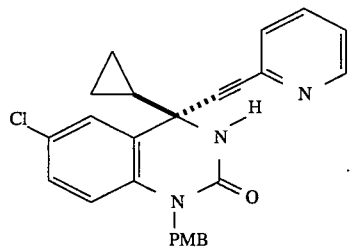

wherein PMB is paramethylbenzyl.

2. The compound

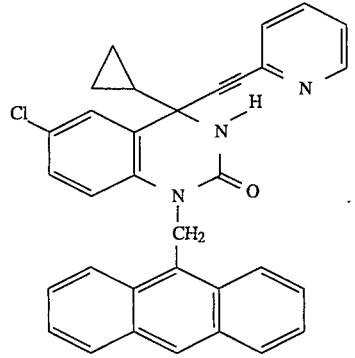

3. The compound
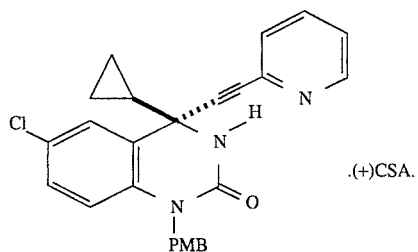
.(+)CSA.
wherein PMB is paramethylbenzyl and (+)-CSA is (1S)-(+)-10-camphorsulphonic acid.
4. The compound
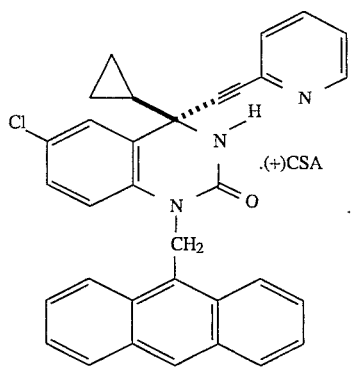
.(+)CSA
wherein (+)-CSA is (1S)-(+)-10-camphorsulphonic acid.
5. The compound
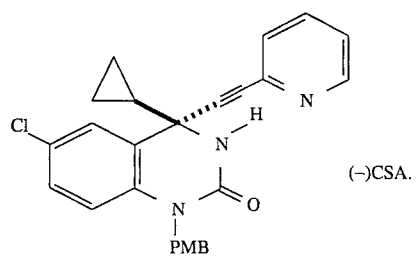
(−)CSA.
wherein (+)-CSA is (1S)-(+)-10-camphorsulphonic acid and wherein PMB is paramethylbenzyl.
6. The compound
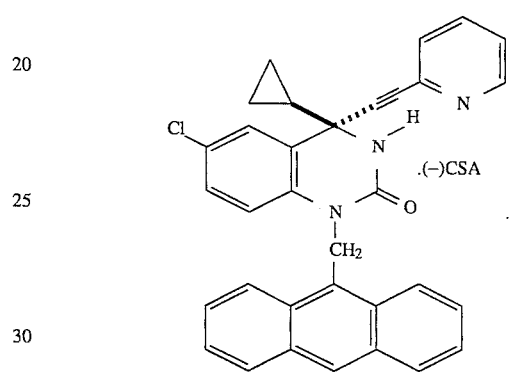
.(−)CSA
wherein (+)-CSA is (1S)-(+)-10-camphorsulphonic acid.
* * * * *